United States Patent
Dubois

(10) Patent No.: US 10,030,255 B2
(45) Date of Patent: Jul. 24, 2018

(54) PROCESS FOR SYNTHESIZING BIFUNCTIONAL HYDROCARBON-BASED COMPOUNDS FROM BIOMASS

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 131 days.

(21) Appl. No.: 14/125,529

(22) PCT Filed: Jun. 8, 2012

(86) PCT No.: PCT/FR2012/051295
§ 371 (c)(1),
(2), (4) Date: Mar. 11, 2014

(87) PCT Pub. No.: WO2012/168668
PCT Pub. Date: Dec. 13, 2012

(65) Prior Publication Data
US 2014/0356918 A1    Dec. 4, 2014

(30) Foreign Application Priority Data
Jun. 10, 2011 (FR) ..................... 11 55110

(51) Int. Cl.
*C12P 7/40* (2006.01)
*C12P 7/42* (2006.01)
*C07C 45/35* (2006.01)
*C07C 51/25* (2006.01)
*C07C 51/377* (2006.01)
*C12P 5/02* (2006.01)
*C12P 7/00* (2006.01)
*C12P 7/04* (2006.01)
*C12P 7/16* (2006.01)
*C12P 7/24* (2006.01)
*C12P 7/28* (2006.01)
*C12P 7/46* (2006.01)
*C12P 7/52* (2006.01)
*C07C 51/23* (2006.01)
*C07C 11/06* (2006.01)
*C07C 45/28* (2006.01)
*C07C 51/16* (2006.01)

(52) U.S. Cl.
CPC ............... *C12P 7/40* (2013.01); *C07C 11/06* (2013.01); *C07C 45/28* (2013.01); *C07C 45/35* (2013.01); *C07C 51/16* (2013.01); *C07C 51/23* (2013.01); *C07C 51/252* (2013.01); *C07C 51/377* (2013.01); *C12P 5/026* (2013.01); *C12P 7/00* (2013.01); *C12P 7/04* (2013.01); *C12P 7/16* (2013.01); *C12P 7/24* (2013.01); *C12P 7/28* (2013.01); *C12P 7/46* (2013.01); *C12P 7/52* (2013.01); *Y02E 50/10* (2013.01)

(58) Field of Classification Search
CPC ..... C07C 45/35; C07C 51/252; C07C 51/377; C07C 51/23; C07C 47/22; C07C 57/04; C07C 11/06; C07C 45/28; C07C 51/16; C12P 5/026; C12P 7/00; C12P 7/04; C12P 7/16; C12P 7/24; C12P 7/28; C12P 7/40; C12P 7/46; C12P 7/52; Y02E 50/10
See application file for complete search history.

(56) References Cited

U.S. PATENT DOCUMENTS
2005/0222458 A1    10/2005    Craciun

FOREIGN PATENT DOCUMENTS

| DE | 197 40 035 C1 | 7/1998 |
|---|---|---|
| FR | 2 952 053 A1 | 11/2009 |
| WO | WO-01/98247 A2 | 12/2001 |
| WO | WO-2007/128941 A2 | 11/2007 |
| WO | WO-2007/137566 A1 | 12/2007 |
| WO | WO-2008/066581 A1 | 6/2008 |
| WO | WO-2009/103026 A1 | 8/2009 |

OTHER PUBLICATIONS

Blaschek H.P. et al., Science of Alternative feedstocks, Chapter 7, Nov. 13, 2007, pp. 112-128, published on the web at—at the web—http://citeseerx.ist.psu.edu/viewdoc/download?doi=10.1.1. 511.1865&rep=rep1&type=pdf.*
Huppmann—Fermentation process with exclusion of atmospheric oxygen, ZA 98/08276 (English equivalent of DE19740035.3; Nov. 9, 1997), 1998, attached pp. 1-17.*
International Search Report, International Application Serial No. PCT/FR2012/051295, dated Sep. 28, 2012.
Song Chunshan, "Global Challenges and Strategies for Control, Conversion and Utilization of C02 for Sustainable Development Involving Energy, Catalysis, Adsorption and Chemical Processing", Catalysis Today, Elsevier, NL, vol. 115, 1-4, Jun. 30, 2006.

* cited by examiner

*Primary Examiner* — Satyendra K Singh
(74) *Attorney, Agent, or Firm* — RatnerPrestia

(57) ABSTRACT

The subject of the present invention is a process for synthesizing bifunctional hydrocarbon-based compounds from biomass, comprising a step of fermentation of the biomass and a step of oxidation of the intermediate compounds resulting from the fermentation step.

21 Claims, No Drawings

PROCESS FOR SYNTHESIZING BIFUNCTIONAL HYDROCARBON-BASED COMPOUNDS FROM BIOMASS

FIELD OF THE INVENTION

The subject of the present invention is a process for synthesizing bifunctional hydrocarbon-based compounds from biomass, comprising a step of fermentation of the biomass and a step of oxidation of the intermediate compounds resulting from the fermentation step.

BACKGROUND OF THE INVENTION

The conventional synthesis of bifunctional hydrocarbon-based compounds, such as unsaturated acids, unsaturated nitriles, acid anhydrides, acetals, aldehydes, epoxides including ethylene oxide and propylene oxide, is carried out industrially via chemical process using raw materials derived from fossil hydrocarbons.

The current change in terms of the environment results, in the energy and chemistry fields, in a preference for the exploitation of natural raw materials originating from a renewable source and also waste. It is the reason why work has been undertaken to industrially develop processes using as raw material products derived from biomass.

Among the conversion processes, fermentation, known for thousands of years and "institutionalized" by Pasteur, has a place of its own and is used only in well-defined industrial sectors; see in this respect the Techniques de l'Ingénieur [Techniques of the engineer] J 6 006, pages 1 to 18. The synthesis of "solvents" such as acetone, butanol and ethanol by fermentation of carbohydrates is well known, mention may particularly be made of U.S. Pat. No. 1,315,585, and has been used industrially since 1919 with a *Clostridium acetobutylicum* bacterium. It should be noted that a bacterium of this genus is used for the synthesis, by fermentation, of acids such as propionic acid, acetic acid and succinic acid (Techniques de l'Ingénieur [Techniques of the engineer] J 6 002, page 9, table 4). From the 1950s onwards, competition for these old processes arrived in the form of chemical processes using oil products, the cost of which was much lower.

In the remainder of the text, the term "bifunctional hydrocarbon-based compounds" is intended to mean compounds with 2 to 6 carbon atoms per molecule comprising two functions, and the term "function" should be understood to mean acid, nitrile, aldehyde, ether or olefinic unsaturation functions. These bifunctional compounds are therefore, for example, diacids, acid anhydrides, unsaturated acids, unsaturated nitriles, unsaturated aldehydes, acetals, diols in the form of epoxide (or oxirane), such as ethylene oxide, propylene oxide, etc., the term "intermediate (fermentation) compounds" is intended to mean saturated acids, hydroxy acids, lactic acid, 3-hydroxypropionic acid, 3-hydroxybutyric acid, 2-hydroxyisobutyric acid, 3-hydroxyisobutyric acid, etc., α-olefins and alcohols, the term "biomass" is intended to mean the biodegradable fraction of products, of waste as defined in European Directive No. 2003/30/EC of 8 May 2003 and which can be converted via fermentation in the presence of microorganisms such as enzymes, bacteria, yeasts, fungi, etc.

The term "biomass" will be intended to mean sugars, starches, celluloses and hemicellulose and any vegetable matter containing sugar, cellulose, hemicellulose and/or starch, and also the syngas.

The vegetable matters containing sugars are mainly sugar cane and sugar beet; mention may also be made, for example, of maple, date palm, sugar palm, sorghum and American aloe.

The vegetable matters containing cellulose and/or hemicellulose are, for example, wood, straw, maize cobs, and seed or fruit oilcakes.

The vegetable matters containing starches are mainly cereals and legumes, wheat, maize, sorghum, rye, rice, potato, cassava, sweet potato, or else algae.

Among the matters derived from recovered materials, mention may be made of plant or organic waste containing sugars and/or starches and/or cellulose, and more generally any fermentable waste, including the syngas derived from natural or industrial processes, and carbon monoxide. The syngas which may be suitable for this type of fermentation can have an $H_2/CO$ molar ratio which varies in a broad range, in particular from 0/1 to 4/1.

The microorganisms used in bioconversion are also well known. These microorganisms depend on the type of biomass to be treated and on the selected mode of fermentation, which may be aerobic or anaerobic. By way of example, mention may be made of alcoholic fermentation with yeasts and bacteria of the *Zymomonas* or *Zymosarcina* genus; homolactic fermentation with bacteria of the *Streptococcus* or *Lactobacillus* genus, heterolactic fermentation with bacteria of the *Leuconostoc* or *Lactobacillus* genus, propionic fermentation with bacteria of the *Clostridium, Propionibacterium* or *Corynebacterium* genus, butyroacetonobutylic fermentation with bacteria of the *Butyribacterium* or *Zymosarcina* genus, mixed acid fermentation with bacteria of the *Escherichia, Salmonella* or *Proteus* genus, and butylene glycol fermentation with bacteria of the *Aerobacter* or *Aeromonas* genus, etc. More recent work has shown that it is possible to introduce improvements into the fermentation processes by successively using two different types of bacteria, which may belong to the same genus, for carrying out the two steps of the overall process, the intermediate step being the synthesis of the acid. In this respect, mention may be made of U.S. Pat. No. 5,753,474 which describes the synthesis of butanol and of similar compounds by fermentation of carbohydrates with bacteria of the *Clostridium* genus, such as *C. tyrobutyricum, C. thermobutyricum, C. butyricum, C. cadaveros, C. cellobioparum*, etc. (column 3, lines 1 to 17). Moreover, even more recent work has shown that it is possible to introduce into certain microorganisms, either by integration within the cell, or by complementary external provision, additional functions capable of improving selectivity and even of allowing new conversions. In this respect, mention may be made of the patent (PCT/FR2009/051332) which describes the synthesis, by fermentation, of terminal alkenes from a carbon source (biomass) by means of a microorganism capable of converting the carbon source into compounds of 3-hydroxyalkanoate type, said microorganism being associated with an enzyme of decarboxylase type which makes it possible to decarboxylate the 3-hydroxyalkanoates formed.

The gas-phase chemical oxidation of olefins, alcohols or acids or aldehydes which are saturated (oxydehydrogenation of alcohols, acids and aldehydes) is also well known.

In the current gas-phase oxidation processes, the compound to be oxidized (alcohol, acid or aldehyde which is saturated, hydrocarbon, etc.) is generally brought into contact with air, very commonly air diluted with nitrogen, in an oxidation reactor. The implementation of this very exothermic reaction is technologically difficult and requires the use of multitubular reactors or fluidized-bed reactors.

Another constraint hangs over oxygen-oxidation reactors, said constraint being linked to the flammability range and therefore to the safety of the processes. It is desirable to be able to operate the reactors outside the flammability zone of the mixtures, for obvious reasons of safety. Unfortunately, this condition limits the operating range, since it is not possible to use large amounts of oxygen or of reagent to be oxidized, in an air-nitrogen-hydrocarbon or air-nitrogen-alcohol ternary mixture, for example.

The solutions usually implemented for avoiding the flammability range consists in diluting the reaction gases either with water vapour, or with recycling gases which are oxygen-depleted (and therefore nitrogen-rich).

It is also known practice to carry out oxidation reactions in the presence of a gas which is inert with respect to the reaction, such as COD, methane, or even propane. The applicant has, in this field, filed two patent applications regarding the partial oxidation, in the gas phase, of light alcohols ($C_1$-$C_4$), methanol in particular, in the presence of a $C_1$-$C_5$ hydrocarbon, methane in particular, for obtaining acetals (WO 07/128941) or light aldehydes (WO 08/007014).

Moreover, it has filed, jointly with the company Air Liquide, a French patent application No. 09 57731 of 2 Nov. 2009 relating to the oxidation of alkenes and in particular of propylene in the presence of propane, published under number WO 11/051621.

In these various cases, both methane and propane acted as a diluent (flammability range) and as a "thermal ballast" (elimination of heat). There are many advantages to adding these types of gases. They have a higher specific heat than nitrogen, they therefore transport more heat from the reactor, they are chemically inert and some inhibit free-radical combustion reactions better, which makes it possible to notably reduce the flammable mixture range and therefore to increase the operating range. The use of a gas ballast of this type therefore makes it possible to increase reactor productivity and/or selectivity. Unfortunately, gases such as methane, $CO_2$ or propane are not already readily available on industrial sites, and their use requires complex recycling/purification processes. In addition, if $CO_2$ was to be specifically produced, from fossil resources, it would contribute to increasing the anthropogenic fossil $CO_2$ emissions of the industrial site, whereas the intention is to limit them.

BRIEF SUMMARY OF THE INVENTION

The purpose of the invention is therefore to manufacture bifunctional hydrocarbon-based compounds of unsaturated acid, unsaturated nitrile, acid anhydride, unsaturated aldehyde, acetal or epoxide type from biomass by therefore dispensing with the use of raw material of fossil origin while at the same time allowing optimization of the operating conditions of the oxidation step.

The invention consists in combining a first step in which, by fermentation of the biomass, intermediate compounds, such as α-olefins, saturated acids, hydroxy acids or alcohols, are formed, with formation of a $CO_2$-rich gas, with a second step for conversion, by means of molecular oxygen in the gas phase, of the intermediate compounds in the presence of the $CO_2$ resulting from the first step.

DETAILED DESCRIPTION OF THE INVENTION

The subject of the invention is a process for synthesizing bifunctional hydrocarbon-based compounds comprising from 2 to 6 carbon atoms per molecule, the two functions being chosen from acid, aldehyde, nitrile, acetal and α-olefinic unsaturation functions, from biomass, consisting, in a first step, in subjecting the biomass to a fermentation in the presence of an appropriate microorganism and/or of an appropriate enzyme allowing the formation of intermediate compounds chosen from saturated acids, optionally bearing a hydroxyl function, alcohols and α-olefins, in liquid or gas form, and also of $CO_2$, and then in a second step, in oxidizing to convert, in the gas phase catalytically using molecular oxygen, the intermediate compounds in the presence of the $CO_2$ resulting from the first step.

The $CO_2$ resulting from the fermentation step can also come from the use of CO, as an inerting gas during anaerobic fermentations.

The functions of the hydrocarbon-based compounds of the invention will be either two acid functions COO, in diacid form or in acid anhydride form, or two functions C—O—C of ether type in acetal form, or two C—O hydroxyl functions or functions in the form of epoxides (ethylene oxide or propylene oxide, etc.), or an acid function and an α-olefinic unsaturation, or an aldehyde function and an α-olefinic unsaturation.

During the first step, an intermediate compound is synthesized by fermentation of the biomass in a known manner, said intermediate compound being either i) an alcohol comprising from 2 to 4 carbon atoms, for example ethanol, propanol, isopropanol, butanol or isobutanol, or ii) an α-olefin comprising from 2 to 4 carbon atoms, for example ethylene, propylene, n-butene or isobutene, or iii) a saturated organic acid, where appropriate bearing a hydroxyl function, comprising 2 to 4 carbon atoms; by way of example of such saturated organic acids, mention may be made of propionic acid, butyric acid, isobutyric acid, lauric acid, 3-hydroxypropionic acid, 2-hydroxyisobutyric acid or 3-hydroxyisobutyric acid and 3-hydroxybutyric acid or a salt of a saturated organic acid, where appropriate bearing a hydroxyl function, comprising 2 to 4 carbon atoms; by way of example of such salts of saturated organic acids, mention may be made of propionic acid salt, butyric acid salt, isobutyric acid salt, lactic acid salt, 3-hydroxypropionic acid salt, 2-hydroxyisobutyric acid salt or 3-hydroxyisobutyric acid salt, and 3-hydroxybutyric acid salt.

Preferably, the cation of the saturated organic acid salt is monovalent and advantageously chosen from sodium, potassium and ammonium.

The biomass denotes the biodegradable fraction of products, waste, etc., of vegetable or animal origin and also the syngases. When subjected to fermentation, it will provide, via the carbon that it contains, the energy required for the growth of the microorganism used and for its conversion into light organic compounds. The biomass according to the invention consists of sugars, starches, celluloses and any vegetable matter containing sugar, cellulose, hemicellulose and/or starch, and also of the syngases. The biomass will preferably contain carbohydrates, sugars containing 5 or 6 carbon atoms (pentoses or hexoses), polyols (glycerol) or biodegradable natural polymers such as starch, cellulose or hemicellulose, or polyhydroxyalkanoates (PHAs) such as PHB (polyhydroxybutyrate) or PHVB (polyhydroxybutyrate-valerate).

The choice of the microorganism(s) used during the first step will depend on the nature of the biomass treated and on the type of intermediate compound desired, which is determined by the compound that is the final objective.

The point common to all these various processes is the concomitant production of $CO_2$.

The fermentation may be anaerobic or aerobic. In the first case of anaerobic fermentation, the latter can in certain cases be carried out in the presence of an inert gas such as, for example, $CO_2$. In the second case, the fermentation is carried out in the presence of molecular oxygen, most commonly provided in the form of air. The gas mixture resulting from the fermentation, whatever its form, will then consist of nitrogen, oxygen, $CO_2$ and other hydrocarbon-based gases, such as olefins or light organic compounds.

When light olefins are produced as intermediate compound, the gas mixture containing both olefins and oxygen may prove to be difficult to handle, in particular owing to flammability risks. These olefins cannot be easily used in direct polymerization, for example, owing to the residual amounts of oxygen. The presence of nitrogen in a large amount can also be detrimental to olefin recovery. On the other hand, when the light olefins, or even the other organic compounds are intended to be oxidized according to the process of the invention, the presence of residual oxygen is not a major drawback.

The intermediate compound is then subjected to an oxidation step by means of molecular oxygen. The oxygen is introduced into the oxidation reactor in the form of air, of pure oxygen or of intermediate air-oxygen mixtures such as enriched air.

The term "oxidation step" should be understood to mean in the broad sense any reaction step involving oxygen as reagent. Thus, oxydehydrogenation is an oxidation within the meaning of the invention, like, moreover, oxydehydration, which is the combination of a dehydration and of an oxidation.

In the process of the invention, the oxidation step is carried out in the presence of the $CO_2$ produced during or else resulting from the first fermentation step. The $CO_2$ present during the oxidation phase performs two functions: that of a "stabilizer", i.e. of an inert gas so as to avoid being under conditions of flammability of the reactive mixture, and that, by virtue of its high specific heat, of an agent for transferring the heat produced during the exothermic oxidation reaction; the latter function is often referred to as "thermal ballast".

By way of examples of schemes of processes in accordance with the invention, fermentation-oxidation coupling, mention may be made, by way of example, of those which involve the following pathways:

Biomass→isopropanol→acrylic acid
Biomass→n-butanol→maleic anhydride/phthalic anhydride
Biomass→isobutanol→methacrylic acid/methyl methacrylate
Biomass→ethanol→acetals
Biomass→butanol→acetals
Biomass→isobutene→methacrylic acid/methyl methacrylate
Biomass→propylene→acrylic acid/acrolein/acrylonitrile/propylene oxide
Biomass→propylene/isobutene→(meth)acrylonitrile
Biomass→propionic acid→acrylic acid
Biomass→lactic acid→acrylic acid
Biomass→3-hydroxypropionic acid→acrylic acid
Biomass→isobutyric acid→methacrylic acid
Biomass→2-hydroxyisobutyric acid or 3-hydroxyisobutyric acid→methacrylic acid The various acids mentioned above can be obtained in their nitrile form by carrying out the final oxidation step in the presence of ammonia.

The step of oxidation in the gas phase of the intermediate compounds is carried out according to the following reaction schemes according to the intermediate compounds and the final products desired.

Alcohol Intermediate Compounds

The oxidation of isopropanol results in acrylic acid according to the succession of reactions which can be carried out in one or more steps:

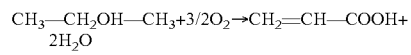

that is to say

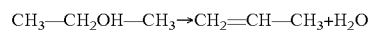

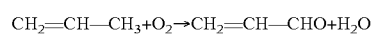

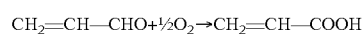

Likewise, the oxidation of isobutanol results in methacrylic acid according to the succession of reactions which can be carried out in one or more steps:

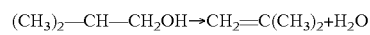

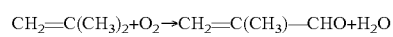

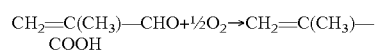

These two reactions in fact comprise two steps with intermediate formation of the aldehyde, acrolein or methacrolein, subsequently oxidized to acid. The oxidation of isopropanol and of isobutanol leads to the aldehyde, acrolein or methacrolein, by oxydehydration, and then subsequently to acrylic acid or methacrylic acid by insertion of oxygen.

The alcohol dehydration step is carried out on an acid catalyst, for example a gamma-alumina, at a temperature of from 200 to 400° C., and preferably in the presence of water vapour.

The olefin oxidation step is carried out in the vapour phase in the presence of air and of water vapour at a temperature of between 300 and 380° C. at low pressure, 1 to 5 bar absolute, in the presence of Mo, Co, Bi and Fe mixed oxide catalysts.

The aldehyde oxidation is carried out under similar conditions, 250<T° C.<350, 1<p<5 bar, in the presence of a catalyst based on Mo and V and optionally W, P, Cu plus, where appropriate, other elements.

The oxidation of n-butanol results in maleic acid and/or the anhydride thereof, which are in equilibrium according to the reactions below.

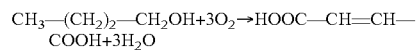

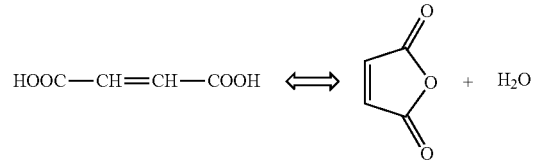 [SMILES: O=C(O)C=CC(=O)O ; O=C1C=CC(=O)O1 ; O]

The oxidation is carried out in the gas phase at a temperature of between 300 and 600° C., at a low pressure of between 1 and 4 bar absolute, in the presence of a catalyst based on vanadium and/or molybdenum oxides. Under certain temperature conditions (low), the formation, following cyclization, of o-phthalic acid or of the anhydride thereof (phthalic anhydride), alongside the maleic compounds, may be noted.

The alcohol oxidation can also be carried out in partial form by working, for example, according to the following reactions.

For the synthesis of light aldehydes from alcohols, the oxydehydrogenation can be carried out according to the following overall reaction process:

R—CH$_2$OH→RCHO+H$_2$ and R—CH$_2$OH+ ½O$_2$→RCHO+H$_2$O or direct oxidation according to the reaction

R—CH$_2$OH+½O$_2$→RCHO+H$_2$O

The synthesis of acetals will be carried out according to the following reaction:

3R—CH$_2$OH+½O$_2$→RCH$_2$—O—RCH—O—CH$_2$R+ 2H$_2$O.

Processes of this type, syntheses, on the one hand, of aldehydes and, on the other hand, of acetals, have, as previously indicated, been described in patent applications WO 2007/034264 and WO 2008/007014 in the name of the applicant.

The synthesis of the aldehyde from the alcohol can thus be carried out either via the route of oxydehydrogenation with a silver metal catalyst at a high temperature of between 500 and 700° C. and at a pressure equal to or slightly above atmospheric pressure, of between 1 and 5 bar, or by direct oxidation, in that case in the presence of catalysts of mixed oxide type, preferably a mixed oxide of molybdenum-vanadium or molybdenum-iron type, at a temperature between 200 and 400° C. at an approximately atmospheric pressure of between 1 and 5 bar.

The direct synthesis of acetals preferably uses as catalyst a mixed oxide of molybdenum-vanadium or molybdenum-iron type as described in application WO 2010/010287 in the name of the applicant. The operating conditions are preferably the following: temperature of between 200 and 300° C. and pressure of between 1 and 5 bar.

A common point between the two applications WO 2007/034264 and WO 2008/007014 is the use of an unreactive light hydrocarbon, in particular methane, for improving the operating and safety conditions of the process.

Olefinic Intermediate Compounds

When, at the end of the first fermentation step the compounds produced are olefins such as ethylene, propylene, n-butene and isobutene, the oxidation thereof is carried out under conditions which are well known since they are already used in industrial processes using oil derivatives as raw material. In this respect, mention may be made of the book *Fundamentals of Industrial Catalytic Processes Chapter 8, Oxidation of Inorganic and Organic Compounds*, C. H. Bartholomew, R. J. Farrauto, 2$^{nd}$ Ed, Wiley Interscience, (2006), pp 578-634.

Propylene is oxidized in the vapour phase successively to acrolein and to acrylic acid according to the following reaction process.

CH$_2$=CH—CH$_3$+O$_2$→CH$_2$=CH—CHO+H$_2$O, then

CH$_2$=CH—CHO+½O$_2$→CH$_2$=CH—COOH.

The first step is carried out at a relatively low temperature, between 300 and 380° C., at a relatively low pressure of between 1 and 5 bar, in the presence of a catalyst consisting of a mixture of mixed oxides containing molybdenum and, optionally, other metals such as Bi, K, Co, Fe, Ni, Sn, Te, W, etc. Use is also made of a diluting gas, generally nitrogen and, optionally, water vapour. The second step is carried out at a slightly lower temperature, between 250 and 350° C., at a pressure of 1 to 5 bar, in the presence of a catalyst based on Mo—V mixed oxides which are generally doped. From an industrial point of view, the two reactions are often carried out within the same reactor comprising two successive zones or in two consecutive reactors, under conditions analogous to those described above for the alcohol oxydehydration.

The process with isobutene is analogous to that of propylene, resulting, in a first step, in methacrolein and then in methacrylic acid in a second, according to the following reactions:

CH$_2$=C(CH$_3$)$_2$+O$_2$→CH$_2$=C(CH$_3$)—CHO+H$_2$O, then

CH$_2$=C(CH$_3$)—CHO+½O$_2$→CH$_2$=CCH$_3$—COOH.

The reactions are carried out at a relatively low temperature, between 300 and 400° C., at a relatively low pressure of between 1 and 5 bar, in the presence of a catalyst consisting of a mixture of mixed oxides (Mo, Bi, K, Co, Fe, etc.) for the first step and of a catalyst based on Mo—V mixed oxides for the second. Generally, in addition to the atmospheric nitrogen and the recycling gas, a diluting gas, generally water vapour, is also used.

The oxidation of n-butene results in maleic anhydride according to the following reaction:

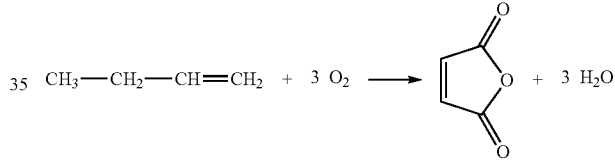

The reaction is carried out in the gas phase at approximately atmospheric pressure and at a temperature of between 350 and 450° C. in the presence of a catalyst consisting of a mixture of molybdenum, vanadium and phosphorus oxides.

Ethylene and propylene can be converted into ethylene oxide or propylene oxide according to the reactions:

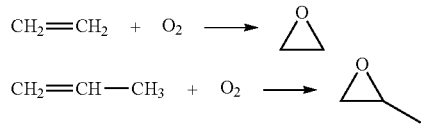

The reactions are carried out at "low" temperature, generally of between 260 and 290° C., by means of a silver catalyst deposited on a sparingly porous support such as α-alumina, aluminosilicates or silicon carbide. From an industrial point of view, obtaining ethylene oxide via this route gives excellent performance levels, but obtaining propylene oxide requires more sophisticated silver catalysts or gold catalysts in order to obtain acceptable yields.

During the step of oxidation of the olefin, propylene or isobutene, it is entirely standard to obtain the corresponding nitriles, acrylonitrile and methacrylonitrile, by ammoxidation reaction (O$_2$+NH$_3$). This reaction applies, moreover, generally to acrolein or methacrolein, whatever its origin.

Saturated Acid Intermediate Compounds

Propionic acid is oxidized to acrylic acid by oxydehydrogenation according to the reaction:

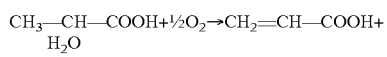
$CH_3\text{—}CH\text{—}COOH + \frac{1}{2}O_2 \rightarrow CH_2\text{=}CH\text{—}COOH + H_2O$ Lactic acid is converted to acrylic acid by dehydration in the presence of oxygen according to the following reaction (the oxygen being used to limit the formation of coke):

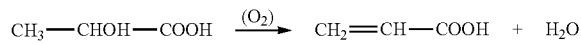
$CH_3\text{—}CHOH\text{—}COOH \xrightarrow{(O_2)} CH_2\text{=}CH\text{—}COOH + H_2O$ 3-Hydroxypropionic acid is converted to acrylic acid according to the same process as lactic acid.

The C4 acids isobutyric acid, 2-hydroxyisobutyric acid and 3-hydroxyisobutyric acid produce methacrylic acid according to oxydehydrogenation and dehydration reaction mechanisms analogous to those of the C3 acids, according to the reactions:

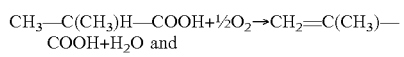
$CH_3\text{—}C(CH_3)H\text{—}COOH + \frac{1}{2}O_2 \rightarrow CH_2\text{=}C(CH_3)\text{—}COOH + H_2O$ and

$CH_3\text{—}C(CH_3)OH\text{—}COOH \rightarrow CH_2\text{=}C(CH_3)\text{—}COOH + H_2O$ and

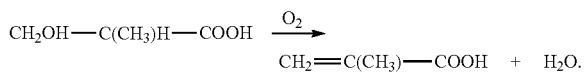
$CH_2OH\text{—}C(CH_3)H\text{—}COOH \xrightarrow{O_2} CH_2\text{=}C(CH_3)\text{—}COOH + H_2O$.

The oxydehydrogenation is carried out in the vapour phase at a temperature of about 400-450° C. with mixed oxide catalysts containing Mo and, optionally, P, V or Fe.

The dehydration is carried out at a temperature generally of between 220 and 400° C., preferably between 250 and 300° C., and at a pressure of between 0.5 and 5 bar. The catalysts are of acid type (Hammett acidity<+2); they will be chosen from siliceous materials, acidic zeolites or mixed oxides such as those based on iron and on phosphorus or those based on cesium, phosphorus and tungsten.

The gas-phase oxidation reaction is carried out on the effluent resulting from the first step. Said effluent, under normal pressure and temperature conditions, is in gas form when the intermediate compound is an olefin, or in liquid form in aqueous solution when the intermediate compound is an alcohol or a saturated acid. In the latter case, the liquid fraction is accompanied by a gas fraction comprising in particular $CO_2$ resulting from the degradation of the carbohydrates subjected to the fermentation. In industrial units implementing this type of fermentation, the $CO_2$ is often used, moreover, as a material for the gasification of beverages.

In the process of the invention, the gas fraction containing the intermediate compound and also the $CO_2$ and other molecules resulting from the fermentation is sent to the oxidation step. According to the operating conditions of the fermentation, for example anaerobic conditions, $H_2$ may be produced, and it will then be necessary to remove this $H_2$ for example by combustion, membrane separation or any other known technique. During aerobic fermentations, the $CO_2$ produced may be present as a mixture with residual oxygen and nitrogen. The mixture may be used directly for the oxidation reaction or may be purified so as to generate a stream enriched in carbon dioxide that would be used for the oxidation reaction.

The oxidation step is carried out by means of molecular oxygen, in the form of air, of $O_2$ enriched air or of pure oxygen. The choice of the form of the oxidizing agent depends in particular on the final products to be synthesized (on the reaction to be carried out), the synthesis of maleic anhydride from n-butene requiring, for example, much more oxygen than the synthesis of ethylene oxide or of propylene oxide.

The gaseous oxidation reaction medium (Medium) will comprise the intermediate compound (Intermediate) to be oxidized, the oxygen (Oxygen) and the "inert" gases, in particular the $CO_2$. The term "inert gases" (Inerts) is intended to mean all the compounds which are not involved in the chemical reaction. Independently of the $CO_2$, nitrogen, argon (if air is used), water vapour, etc., may be found.

The content of these various constituents will be such that the Oxygen/Intermediate ratio will be between 1/12 and 6/1, preferably between 1/6 and 4/1, the Intermediate/Medium ratio between 1% and 40% and preferably between 3% and 20%, the Inert content of the Medium between 40% and 90% and preferably between 60% and 80%, the $CO_2$/Inert ratio between 50% and 90%, and the nitrogen content of the Inert between 1% and 50% and in stabilized operation (after starting the equipment), preferably between 1% and 20%.

When the intermediate compound is in liquid form, the $CO_2$ resulting from the first step is captured so as to be used during the oxidation step. It may be used to strip this intermediate compound before conveying it to the oxidation reactor. It may also be sent to the oxidation reactor independently of the liquid intermediate compound that will be extracted from the medium of the first step by any suitable means.

The $CO_2$-rich gas stream is optionally purified (by any technique known to those skilled in the art) before being conveyed to the oxidation reactor in order to remove the compounds that may possibly be detrimental to said oxidation (hydrogen, sulphur-containing compounds, etc.).

In one variant of the process, the oxidation is carried out with "pure" oxygen in order to limit the amount of nitrogen, an inert gas which is not very efficient in extracting the heat produced during the reaction. In order to ensure a sufficient volume of inert gas, both to take the reaction medium out of the flammable zone and to ensure extraction of the heat, all or part of the noncondensable, $CO_2$-rich gases resulting from the oxidation reactor may also be recycled.

As has been previously indicated, the gas-phase oxidation reactions generally use multitubular reactor or fluidized-bed reactor technologies. When the reactor technology selected uses multitubular reactors, the temperature within the reactor is not uniform. There are hot spots, linked to the difficulties in evacuating the heat from the reaction within the reactor. When fluidized-bed reactors are used, the temperature is more homogeneous than in the previous case since the catalyst transports a part of the heat throughout the reactor. However, in both the reactor configurations, the gas transports a considerable part of the reaction heat.

In order to remove this heat, in the case of multitubular reactors, a heat-transfer fluid, often molten salts such as mixtures of $NaNO_2$, $NaNO_3$ and $KNO_3$, which transfer a large part of the heat from the reaction to a boiler which produces vapour under pressure, is circulated between the tubes. In the case of fluidized-bed reactors, cooling hair pins can be inserted in the catalytic bed in order to extract part of the reaction heat. Nevertheless, these reactor technologies, which are well known to those skilled in the art, remain limited by their capacity to efficiently manage the reaction heat via their limited heat-exchange surface, and consequently are limited in terms of productivity. Solutions for increasing the production of desired product without increasing the size or the weight of the reactors are therefore sought. In increasing reactor productivity it is also sought to limit fossil CO, emissions linked to industrial activities, so as to make industrial production more compliant with sustainable development.

The use of inert gases with a high heat capacity in place of nitrogen makes it possible to manage the heat extraction better and therefore to have better control of the temperature in the reactor. In the process of the invention, the use of the carbon dioxide produced during the first step has the advantage of improving the overall performance levels of the unit while at the same time avoiding the release of this highly detrimental gas.

The process of the invention makes it possible in particular to produce "biobased" products, i.e. products synthesized from non-fossil natural products, the vegetable or animal origin of which was the opportunity to fix the $CO_2$ giving the whole a particularly satisfactory balance.

It is entirely possible to control the "biobased" nature of the raw materials used at the level of the manufactured products.

The term ""biobased" synthesized product (acid, anhydride, nitrile, acetal, oxide)" is intended to mean a compound which has a $^{14}C$ carbon content characteristic of the nonfossil natural origin of the raw materials used.

The use of carbon-based raw materials of natural and renewable origin can be detected by virtue of the carbon atoms which are part of the composition of the final product. Indeed, unlike materials derived from fossil materials, materials composed of renewable raw materials contain $^{14}C$. All carbon samples taken from living organisms (animal or vegetable) are in fact a mixture of three isotopes: $^{12}C$ (representing ~98.892%), $^{13}C$ (~1.108%) and $^{14}C$ (traces: $1.2 \times 10^{-10}$%). The $^{14}C/^{12}C$ ratio of living tissues is identical to that of the atmosphere. In the environment, $^{14}C$ exists in two predominant forms: in inorganic form, i.e. in the form of carbon dioxide ($CO_2$), and in organic form, i.e. in the form of carbon integrated into organic molecules.

In a living organism, the $^{14}C/^{12}C$ ratio is kept constant by the metabolism since the carbon is continually exchanged with the environment. Since the proportion of $^{14}C$ is approximately constant in the atmosphere, the same is true in the organism, as long as it is alive, since it absorbs this $^{14}C$ as it absorbs $^{12}C$. The average $^{14}C/^{12}C$ ratio is equal to $1.2 \times 10^{-12}$.

$^{12}C$ is stable, i.e. the number of atoms of $^{12}C$ in a given sample is constant over time. $^{14}C$ is itself radioactive and each gram of carbon of a living being contains sufficient $^{14}C$ isotope to give 13.6 disintegrations per minute.

The $T_{1/2}$ half-life (or period), linked to the disintegration constant of $^{14}C$, is 5730 years. Given this duration, it is considered that the $^{14}C$ content is virtually constant from the extraction of the vegetable raw materials to the manufacture of the final product.

At the current time, there are at least two different techniques for measuring the $^{14}C$ content of a sample:
- by liquid scintillation spectrometry;
- by mass spectrometry: the sample is reduced to graphite or to $CO_2$ gas, analyzed in a mass spectrometer. This technique uses an accelerator and a mass spectrometer to separate the $^{14}C$ ions from the $^{12}C$ ions and therefore determines the ratio of the two isotopes.

These methods for measuring the $^{14}C$ content of materials are described precisely in the ASTM D 6866 standards (in particular D6866-06) and in the ASTM D 7026 standards (in particular 7026-04). The method of measurement preferentially used is mass spectrometry described in the ASTM D6866-06 standard ("accelerator mass spectroscopy").

The subject of the invention is a process for "biobase" products having a weight content of $^{14}C$ such that the $^{14}C/^{12}C$ ratio is between $0.2 \times 10^{-12}$ and $1.2 \times 10^{-12}$. Preferably, the $^{14}C/^{12}C$ ratio is between $0.6 \times 10^{-12}$ and $1.2 \times 10^{-12}$ and more preferably between $0.9 \times 10^{-12}$ and $1.2 \times 10^{-12}$.

The $^{14}C/^{12}C$ ratio will be dependent on the manufacturing methods implemented, on the raw materials used, which are completely or partially of nonfossil natural origin, or according to subsequent mixtures made. This ratio cannot exceed $1.2 \times 10^{-12}$; should this be the case, it would imply that the operator has artificially introduced the $^{14}C$ atoms into the compound produced.

EXAMPLES

The process of the invention will be illustrated by the examples hereinafter.

These examples describe and illustrate the formation of propylene, of isobutene and of ammonium lactate from biomass and the influence of $CO_2$ on the second step of propylene, isobutene or ammonium lactate oxidation.

Example 1: Manufacture of Propylene from Wheat Straw by Enzymatic Hydrolysis Followed by Acetone/Butanol Fermentation and then by Hydrogenation of Acetone This step is carried out as described in the Revue de l'Institut Français du Pétrole [Journal of the French Oil Institute], Vol 36, No. 3, May-June 1981, pages 339-347.

Wheat straw is shredded in a shredder and then the shredded straw is ground in a hammer mill. The ground straw is then treated with acid at low concentration at a temperature of 100° C. for approximately 1 hour.

After neutralization of the acid, the medium is brought back to a pH in the vicinity of 5 which is required by enzymatic hydrolysis.

A cellulase solution is prepared in the presence of nutrient elements in fermenters in series, the culturing of the *Trichoderma reesei* microorganism being carried out in the first fermenters starting from preground straw, and the cellulase being produced in the following fermenters. The desired enzymatic solution is separated from the contents of the final fermenter by centrifugation and filtration.

An enzymatic hydrolysis of the above pretreated straw is carried out with the above enzymatic solution in reactors arranged in series.

After filtration, solutions of $C_6$ and $C_5$ sugars are collected. The filtrate, which contains lignin is dried in order to be used as fuel.

An acetone/butanol fermentation of the above solutions of $C_6$ and $C_5$ sugars is then carried out using the *Clostridium acetobutylicum* microorganism under aseptic conditions.

The fermentation comprises two successive phases, the first resulting in the production of acetic and butyric acids and the second resulting in the production of acetone, butanol and ethanol in the following proportions by weight: butanol 68%; acetone 29%; and ethanol 3%.

The acetone is separated by azeotropic distillation.

The $CO_2$ produced during the fermentation is recovered and isolated from the other gases (in particular hydrogen) by absorption in potassium hydroxide. The $CO_2$ is thus produced to measure for the oxidation reaction by desorption from the potassium hydroxide.

After azeotropic distillation, the acetone is recovered and hydrogenation of the acetone to isopropanol is carried out.

After separation of the isopropanol from the other compounds, the isopropanol is injected, in order to carry out the dehydration thereof, into a tubular reactor with a diameter of 127 mm, under vacuum (pressure of approximately 0.8 bar), at a temperature of 345° C., containing a catalytic bed consisting of a layer of ESM110® alumina from Eurosupport, the hourly space velocity (ratio of the flow rate by volume of acetone to the volume of catalyst) being 1 $h^{-1}$.

The mixture of water and propylene produced in the reactor is cooled in a heat exchanger, before being conveyed to a gas-liquid separator where the propylene and the water are separated.

A propylene purification step is performed before carrying out the second oxidation step, while condensing the residual traces of organic compounds (acetone, isopropanol, ether, etc.) in the propylene.

Example 2: Oxidation of Propylene in the Presence of $CO_2$

A tubular reactor with an internal diameter of 25.4 mm and a length of 3 mm is filled with ACF7 commercial catalysts from Nippon Shokubai, arranged in series with another tubular reactor with the same diameter and with a length of 2.4 m and filled with ACS7 commercial catalysts from Nippon Shokubai. The tubes are equipped with a multipoint thermocouple at their centre for direct reading of a temperature profile.

The reactors are of molten salt bath type, the stirring of the salt being performed by bubbling nitrogen into the molten salt. The first reactor was charged with 315 g of ACF7L catalyst at the top (i.e. 438 ml) and 773 g of ACF7S at the bottom (i.e. 1023 ml), representing respectively 0.9 m and 2.1 m of tube length. The second reactor was charged with 508 g of ACS7L catalyst at the top (i.e. 438 ml) and 935 g of ACS7S at the bottom (i.e. 731 ml), representing respectively 0.9 m and 1.5 m of tube length.

The composition of the gas feeding the first reactor is an $O_2$/propylene/$N_2$/$CO_2$ mixture (use of air diluted with nitrogen) with the $CO_2$ content being varied from 0 to 66%, by replacing the nitrogen with $CO_2$.

The $CO_2$ content in the gas is gradually increased, with holds of 8 hours being performed for each level of $CO_2$ concentration, up until the highest concentration (66%), at which a hold of 20 h is performed while performing balances. The latter show reproducibility of the results over the course of this period.

TABLE 1

| | Test without $CO_2$ added | Test with 66% of $CO_2$ |
|---|---|---|
| Reactor 1 | | |
| Age (h) | 801 | 622 |
| Salt temperature (° C.) | 320 | 324 |
| Hot spot temperature (° C.) | 381 | 362 |
| Reactor 2 | | |
| Salt temperature (° C.) | 278 | 270 |
| Hot spot temperature (° C.) | 332 | 352 |
| Feed conditions | HSV: 1560 $h^{-1}$ 6.9% propylene, 8.4% $H_2O$, $O_2$/propylene = 1.95 | HSV: 1560 $h^{-1}$ 9.0% propylene, 8.4% $H_2O$, $O_2$/propylene = 1.8 |

TABLE 1-continued

| | Test without $CO_2$ added | Test with 66% of $CO_2$ |
|---|---|---|
| $CO_2$ (%) in feed | 0 | 66 |
| Carbon balance (%) | 100 | 98 |
| Oxygen balance (%) | 105 | 102 |
| Residual oxygen at Reactor 2 outlet (%) | 3.7 | 2.8 |
| Yields (outlet 2° stage) (%) | | |
| Acrylic acid | 86.1 | 85.5 |
| Acrolein | 0.27 | 0.34 |
| Acetic acid | 2.3 | 2.0 |
| Acetaldehyde | 0.04 | 0.02 |
| $CO_2$ | 4.15 | 5.5 |
| CO | 2.06 | 1.6 |
| Conversion of propylene (%) | 96.4 | 96.7 |
| Propionic acid/acrylic acid | 370 ppm | 269 ppm |
| Pressure drop over reactor 1 | 181 mbar | 158 mbar |
| Pressure drop over reactor 2 | 140 mbar | 138 mbar |
| Observation | The first reactor exhibits a double hot spot, in each layer of catalyst. The second stage exhibits a very marked hot spot in the first layer of catalyst. | The temperature profile of the first reactor is much flatter. On the other hand, the temperature profile over the second stage is much more marked. |

The results in table 1 illustrate that, in the presence of added $CO_2$, the productivity of the reactor is significantly improved, since there is a change from 298 g of acrylic acid per liter of catalyst and per hour to 386 g of acrylic acid per liter of catalyst and per hour. This result is explained in particular by the possibility of increasing the partial propylene pressure in the feed, without risking a runaway of the reactor.

The temperature profiles noted on the two reactors illustrate the fact that the reaction on the first reactor is much better controlled: it is highly likely that less acrylic acid is produced on the first reactor in the presence of $CO_2$ compared with the case where air is the oxidizing agent, and that, consequently, the rest of the conversion of the acrolein is carried out on the second reactor.

A better control of the temperature profile on the first-stage reactor should result in a gain in lifetime of the catalyst.

Example 3: Oxidation of Propylene to Acrolein in the Presence of $CO_2$

Example 2 is reproduced, but with the reaction conditions being modified and with the second stage not being used.

TABLE 2

| | Test without $CO_2$ added | Test with 66% of $CO_2$ |
|---|---|---|
| Reactor 1 | | |
| Age (h) | 506 | 580 |
| Salt temperature (° C.) | 319 | 327 |
| Hot spot temperature (° C.) | 391 | 365 |
| Feed conditions | HSV: 1560 $h^{-1}$ 6.9% propylene, 8.4% $H_2O$, $O_2$/propylene = 1.35 | HSV: 1560 $h^{-1}$ 9.0% propylene, 8.4% $H_2O$, $O_2$/propylene = 1.3 |

TABLE 2-continued

|  | Test without $CO_2$ added | Test with 66% of $CO_2$ |
|---|---|---|
| $CO_2$ (%) in the feed | 0 | 66 |
| Carbon balance (%) | 97 | 96 |
| Oxygen balance (%) | 103 | 101 |
| Residual oxygen at reactor 2 outlet (%) | 3.1 | 2.7 |
| Yields (outlet 1° stage) (%) | | |
| Acrylic acid | 10.6 | 7.3 |
| Acrolein | 80.3 | 85.2 |
| Acetic acid | 0.3 | 0.3 |
| Acetaldehyde | 0.7 | 0.6 |
| $CO_2$ | 1.9 | 1.7 |
| CO | 0.9 | 0.8 |
| Conversion of propylene (%) | 96.0 | 95.5 |
| Observation | The reactor exhibits a double hot spot, in each layer of catalyst. | The temperature profile of the reactor is much flatter. |

According to this example, it is possible to take advantage of the gain provided by the use of $CO_2$ in this reaction in order to obtain a gain in selectivity.

Example 4: Oxidation of Isobutene in the Presence of $CO_2$

Crude renewable isobutanol resulting from fermentation and containing 50% by weight of water and 4% by weight of ethanol is sent to a dehydration reactor containing a Siralox 40/450 silica-alumina, maintained at 300° C. The reaction products are separated in a gas/liquid separator in order to condense the water produced at 0° C. and also the unreacted isobutanol. The gas mixture is then sent to an oxidation reactor 15 mm in diameter and 50 cm in length. The gas rich in $CO_2$ produced during the fermentation is used to dilute the reaction gases.

Although it is not the ideal catalyst, the ACF7S catalyst described in example 2 is used for this example.

TABLE 3

|  | Test without $CO_2$ added, but with nitrogen | Test with 55% of $CO_2$ |
|---|---|---|
| Reactor 1 | | |
| Age (h) | 200 | 300 |
| Salt temperature (° C.) | 325 | 330 |
| Hot spot temperature (° C.) | 380 | 365 |
| Feed conditions | HSV: 1500 h$^{-1}$ 5% isobutene, 8.4% H$_2$O, O$_2$/isobutene = 1.5 | HSV: 1500 h$^{-1}$ 5.0% isobutene, 8.4% H$_2$O, O$_2$/isobutene = 1.45 |
| $CO_2$ (%) in the feed | 0 | 55 |
| Carbon balance (%) | 95 | 96 |
| Oxygen balance (%) | 101 | 104 |
| Yields (outlet 1° stage) (%) | | |
| Methacrylic acid | 12.5 | 11.2 |
| Methacrolein | 35.2 | 45.3 |

Example 5: Dehydration of Ammonium Lactate in the Presence of $CO_2$

The ammonium lactate is prepared by anaerobic fermentation of dextrose while controlling the fermentation atmosphere by feeding the fermentation reactor with $CO_2$ generated during an alcoholic fermentation (ethanol production). The pH of the medium is controlled during the fermentation by continuously adding aqueous ammonia to the medium, in order to maintain a neutral pH. At the end of the fermentation, the ammonium lactate is recovered by filtration (in order to separate it from the microorganisms). The medium is then concentrated to a content of 30% by weight.

The aqueous solution of ammonium lactate will be used in a dehydration reactor.

The gas leaving the fermentation reactor is a gas which is rich in $CO_2$ but contains some impurities, in particular ammonia, water vapour and nitrogen. This gas will constitute the fluidizing gas during the dehydration of the ammonium lactate.

A fluidized-bed pilot reactor is used to carry out the dehydration of the ammonium lactate. The dimensions of the reactor are a diameter of 5 cm and a height of 75 cm. The gas is introduced at the bottom of the reactor in order to ensure fluidization of 300 g of catalyst. The catalyst selected is a hydroxyapatite (calcium phosphate hydrate) having a P/Ca molar ratio of 1.6. The reaction temperature is 320° C. The aqueous solution of ammonium lactate is fed by means of a nebulizer just above the distribution grid at the bottom of the reactor. The molar composition of the reaction mixture is adjusted so as to have 4 mol % of ammonium lactate, and 1 mol % of oxygen, with the rest being gas rich in $CO_2$ originating from the fermentation.

The acrylic acid yield obtained is 37%.

When the gas originating from the fermentation is replaced with pure nitrogen, the acrylic acid yield is then 26%.

Example 6: Oxidation of Isobutene in the Presence of $CO_2$ with Another Catalyst Gamma-alumina catalyst from Sasol, of Puralox SCCa 150/200 type, which has a silica content of 0.03% by weight and an iron oxide content of 0.02% by weight, and a specific surface area of 200 m$^2$/g, is used. This alumina is in the form of a powder which has an average particle size of 150 microns and can be used directly.

A tubular reactor with an internal diameter of 10 mm is charged with 10 grams of catalyst. The reactor is fed with a mixture of isobutanol/water (which result from a fermentation process) having a ratio of 95/5 with a flow rate of 1.2 g of isobutanol per minute. The total HSV is 2650 h$^{-1}$ for this reaction carried out in the gas phase. The reactor is maintained at 325° C. At the reactor outlet, the gas produced is combined with the $CO_2$-rich gases resulting from the fermentation, and a reactor for oxidation of the isobutene is fed as in example 4.

The composition of the gas mixture is 4% of isobutene, 6% of oxygen and 40% of $CO_2$. The methacrolein yield is 40%.

When the $CO_2$ is replaced with nitrogen, the methacrolein yield is 36%.

Example 7: Oxidation of Isobutanol from Fermentation, in the Presence of $CO_2$ from Fermentation, with Another Catalyst The reaction is carried out in the presence of a commercial catalyst of iron molybdate type, MFM3-MS supplied by Mapco, having an Mo/Fe atomic ratio of 2.5, were mixed with 300 mg of silicon carbide and charged to the reactor.

Catalyst MFM3-MS: external diameter=3.9 mm, internal diameter=1.85 mm, height=4.04 mm.

The catalyst is first of all activated under a stream of helium/oxygen (48 Nml/min-12 Nml/min) at 300° C. for 15 hours and 30 minutes. The temperature is then brought back to 250° C. and the data acquisition begins. After stabilization, the performance levels of the catalyst are recorded. The temperature of the catalyst is then increased in stages and at each level (260, 280 and 300° C.), data are recorded.

The oxygen and helium flow rates are, respectively, 6.7 and 26.4 Nml/min and the isobutanol concentration is adjusted to 5% (conditions: isobutanol/$O_2$/helium/$CO_2$ from fermentation: 5/13/82/0 for an HSV of 10 000 ml·h$^{-1}$·g$^{-1}$).

The results in terms of conversions and selectivities obtained during the catalytic oxidation of the isobutanol are reported in table 4 (IBAL=isobutyraldehyde; MAL=methacrolein; MAA=methacrylic acid).

TABLE 4

| Catalyst | Temperature (° C.) | Conversion (%) | Selectivities (%) | | |
|---|---|---|---|---|---|
| | | | IBAL | MAL | MAA |
| MFM3-MS | 250 | 20 | 20 | 25 | 3 |
| | 260 | 25 | 16 | 30 | 4 |
| "FeMo" | 280 | 33 | 10 | 35 | 5 |
| | 300 | 56 | 7 | 37 | 7 |

The previous example is reproduced with, this time, $CO_2$ resulting from the fermentation having resulted in the isobutanol production.

Conditions: isobutanol/$O_2$/helium/$CO_2$ from fermentation: 5/13/20/62 for an HSV of 10 000 ml·h$^{-1}$·g$^{-1}$. The results in terms of conversions and selectivities obtained are reported in table 5.

TABLE 5

| Catalyst | Temperature (° C.) | Conversion (%) | Selectivities (%) | | |
|---|---|---|---|---|---|
| | | | IBAL | MAL | MAA |
| MFM3-MS | 260 | 27 | 14 | 37 | 4 |
| "FeMo" | 300 | 60 | 6 | 42 | 6 |

What is claimed is:

1. A process for synthesizing bifunctional hydrocarbon-based compounds comprising two functions and from 2 to 6 carbon atoms per molecule, the two functions being selected from the group consisting of acid, aldehyde, nitrile, acetal and α-olefinic unsaturation functions, from a biomass, the process comprising:
   in a first step, subjecting the biomass to a fermentation in the presence of an appropriate microorganism and/or of an appropriate enzyme thereby forming i) one or more intermediate compounds selected from the group consisting of saturated organic acids, salts of saturated organic acids, alcohols and α-olefins, in liquid or gas form, and ii) $CO_2$, and then
   in a second step, converting, in a gas phase catalytically using molecular oxygen and one or more catalysts comprising a metal, the intermediate compounds in the presence of the $CO_2$ resulting from the first step into the bifunctional hydrocarbon-based compounds comprising two functions and from 2 to 6 carbon atoms per molecule, the two functions being selected from the group consisting of acid, aldehyde, nitrile, acetal and α-olefinic unsaturation functions;
   wherein in the second step, a gaseous oxidation reaction medium (Medium) comprising the intermediate compounds (Intermediate), oxygen (Oxygen), and one or more inert gases (Inert) is fed to a reactor in which the converting takes place, the content of the various constituents of the Medium being such that the Oxygen/Intermediate ratio is between 1/12 and 6/1, the Intermediate/Medium ratio is between 1% and 40%, the Inert content of the Medium is between 40% and 90%, the $CO_2$/Inert ratio is between 50% and 90% and the nitrogen content of the Inert is between 1% and 50%; and
   wherein
   a) when the one or more intermediate compounds is or are one or more α-olefins, the second step is carried out at a relatively low temperature between 300 and 380° C. at a pressure of between 1 and 5 bar in the presence of a catalyst consisting of a mixture of mixed metal oxides;
   b) when the one or more intermediate compounds is or are one or more saturated organic acids, the second step is carried out in the vapour phase at a temperature of about 400-450° C. with one or more mixed oxide catalysts containing Mo and, optionally, one or more of P, V or Fe.

2. The process according to claim 1, wherein the intermediate compounds include an alcohol comprising from 2 to 4 carbon atoms.

3. The process according to claim 1, wherein the intermediate compounds include an α-olefin comprising from 2 to 4 carbon atoms.

4. The process according to claim 1, wherein the intermediate compounds include a saturated organic acid comprising from 2 to 4 carbon atoms.

5. The process according to claim 1, wherein the intermediate compounds includes a salt of a saturated organic acid comprising 2 to 4 carbon atoms.

6. The process according to claim 4, wherein the saturated organic acid comprises a hydroxyl function.

7. The process according to claim 5, wherein the salt of the saturated organic acid comprises a hydroxyl function.

8. The process according to claim 1, wherein the biomass contains one or more substances selected from the group consisting of sugars, starches, celluloses, and vegetable matter containing sugar, cellulose, hemicellulose and starch.

9. The process according to claim 1, wherein the biomass contains one or more substances selected from the group consisting of carbohydrates, sugars containing 5 or 6 carbon atoms, polyols, biodegradable natural polymers, and polyhydroxyalkanoates (PHAs).

10. The process according to claim 1, wherein the fermentation is anaerobic.

11. The process according to claim 1, wherein the fermentation is aerobic.

12. The process according to claim 1, wherein the second step is carried out with molecular oxygen introduced into the reactor in the form of air, pure oxygen or an intermediate air-oxygen mixture.

13. The process according to claim 1, wherein the content of the various constituents of the Medium is such that the Oxygen/Intermediate ratio is between 1/6 and 4/1, the Intermediate/Medium ratio is between 3% and 20%, the Inert content of the Medium is between 60% and 80%, the $CO_2$/Inert ratio is between 50% and 90% and the nitrogen content of the Inert is between 1% and 20% in stabilized operation.

14. The process according to claim 1, wherein the intermediate compounds include at least one of a saturated organic acid bearing a hydroxyl group or a salt of a saturated organic acid bearing a hydroxyl group.

15. The process according to claim 1, wherein the intermediate compounds comprise an alcohol.

16. The process according to claim 15, wherein the alcohol is ethanol, propanol, isopropanol, butanol or isobutanol.

17. The process according to claim 1, wherein the two functions are acid functions.

18. The process according to claim 1, wherein the two functions are aldehyde functions.

19. The process according to claim 1, wherein the two functions are nitrile functions.

20. The process according to claim 1, wherein the two functions are acetal functions.

21. The process according to claim 1, wherein the two functions are α-olefinic unsaturation functions.

* * * * *